(12) United States Patent
Dharia et al.

(10) Patent No.: US 8,968,663 B2
(45) Date of Patent: Mar. 3, 2015

(54) MONITORING MEMBRANE-BOUND PROTEINS

(75) Inventors: Sameera Dharia, San Diego, CA (US); Richard D. Rabbitt, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 922 days.

(21) Appl. No.: 13/154,870

(22) Filed: Jun. 7, 2011

(65) Prior Publication Data

US 2012/0267260 A1    Oct. 25, 2012

Related U.S. Application Data

(60) Provisional application No. 61/517,809, filed on Apr. 25, 2011.

(51) Int. Cl.
| | |
|---|---|
| *G01N 15/06* | (2006.01) |
| *G01N 33/00* | (2006.01) |
| *G01N 33/48* | (2006.01) |
| *G01N 33/487* | (2006.01) |

(52) U.S. Cl.
CPC .............................. *G01N 33/48728* (2013.01)
USPC ...... 422/82.01; 422/50; 422/68.1; 422/82.02; 436/43; 436/63; 436/149

(58) Field of Classification Search
USPC ......... 422/50, 68.1, 82.01, 82.02; 436/43, 63, 436/149
See application file for complete search history.

(56) References Cited

U.S. PATENT DOCUMENTS

2003/0054431 A1* 3/2003 Raguse et al. ................... 435/25
2009/0288960 A1* 11/2009 Rubin et al. ................ 205/777.5

OTHER PUBLICATIONS

Ackerman et al; Ion Channels—Basic Science and Clinical Disease; Mechanisms of Disease; May 29, 1997; pp. 1575-1586; vol. 336, No. 22.
Ayliffe et al; Electric Impedance Spectroscopy Using Microchannels with Integrated Metal Electrodes; IEEE Journal of Microelectromechanical Systems; Mar. 1999; pp. 50-57; vol. 8, No. 1.
Becker et al.; Separation of Human Breast Cancer Cells From Blood by Differential dielectric Affinity; Proc. Natl. Acad. Sci.; Jan. 1995; pp. 860-864; vol. 92.
Cheung et al; Impedance Spectroscopy Flow Cytometry: On-Chip Label-Free Cell Differentiation; Cytometry Part A; 2005; pp. 124-132; vol. 65A.

(Continued)

*Primary Examiner* — Brian J Sines
(74) *Attorney, Agent, or Firm* — Thope North & Western LLP (57) ABSTRACT

An apparatus for examining membrane-bound proteins in a cell can include a chamber with an insulating partition dividing the chamber into an upper well and a lower well, and a pore penetrating the insulating partition. The pore can have a size and shape so as to snugly hold a cell in place therein. The apparatus can further include circuitry for delivering a radio frequency signal to the cell. A belt electrode for delivering electrical signals to the cell can be located within the insulation partition and substantially encircling the pore. A measuring circuit for measuring cell membrane impedance to the radio frequency signal is also provided, and changes in the impedance can signal a change in state of a protein in the cell membrane.

19 Claims, 11 Drawing Sheets

(56) References Cited

OTHER PUBLICATIONS

Dharia et al; Monitoring Voltage-Dependent Charge Displacement of Shaker B-IR K+ Iong Channels Using Radio Frequency Interrogation; PLoS One; Feb. 2011; pp. 1-8.
Dharia et al; Monitoring Voltage-Sensitive Membrane Impedance Change Using Radio Frequency Interrogation; Conf Proc IEEE Eng Med Biol Soc.; 2010; pp. 889-894.
Dharia et al; Single Cell Electric Impedance Topography: Mapping Membrane Capacitance; Lab on a Chip; 2009; pp. 3370-3377; vol. 9.
Dharia; Spatially and Temporally Resolving Radio-Frequency Changes in Effective Cell Membrane Capacitance; May 2011; 149 pages.
Dittami et al.; A Multilayer MEMS Platform for Single-Cell Electric Impedance Spectroscopy and Electrochemical Analysis; J. Microelectromech Syst.; Sep. 14, 2009; 31 pages.
Dittami et al.; Electrically Evoking and Electrochemically Resolving Quantal Release on a Microchip; Lab Chip; 2010; pp. 30-35; vol. 10.
Ehret et al; Monitoring of Cellular Behaviour by Impedance measurements on Interdigitated Electrode Structures; Biosensors & Bioelectronics; 1997; pp. 29-41; vol. 12, No. 1.
Elinder et al.; Metal Ion Effects on Ion Channel Gating; Quarterly Reviews of Biophysics; 2004; pp. 373-427; vol. 36, No. 4.
Gawad et al; Micromachined Impedance Spectroscopy Flow Cytometer for Cell Analysis and Particle Sizing; Lab on a Chip; 2001; pp. 76-82; vol. 1.
Gritsch et al; Impedance Spectroscopy of Porin and Gramicidin Pores Reconstituted into Supported Lipid Bilayers on Indium-Tin-Oxide Electrodes; Langmuir; 1998; pp. 3118-3125; vol. 14.
Han et al.; Ion Channels Characterization Using Single Cell Impedance Spectroscopy; Lab on a Chip; 2006; pp. 1412-1414; vol. 6.
Han et al.; Microsystems for Isolation and Electrophysiological Analysis of Breast Cancer Cells form Blood; Biosensors and Bioelectronics; 2006; pp. 1907-1914; vol. 21.
Hoffman et al; Flow-System Measurement of Cell Impedance Properties; The Journal of Histochemistry and Cytochemistry; 1979; pp. 234-240; vol. 27, No. 1.
Hoshi et al; Biophysical and Molecular Mechanism of Shaker Potassium Channel Inactivation; Science; Oct. 26, 1990; pp. 533-538; vol. 250, No. 4980.
Huang et al.; Membrane Dielectric Responses of Human T-Lymphocytes Following Mitogenic Stimulation; Biochimica et Biophysica Acta; 1999; pp. 51-62; vol. 1417.
Hubner et al; Ion Channel Diseases; Human Molecular Genetics; 2002; pp. 2435-2445; vol. 11, No. 20.
Kalinowski et al; A Four-Electrode Potentiostat-Galvanostat for Studies of Bilayer Lipid Membranes; Meas. Sci. Technol.; 1995; pp. 1050-1055; vol. 6.
Keese et al.; A Biosensor That Monitors Cell Morphology with Electrical Fields; IEEE Engineering in Medicine and Biology; Jun./Jul. 1994; pp. 402-408.
Lehmann-Horn et al; Voltage-Gated Ion Channels and Hereditary Disease; Physiological Reviews pp. 1317-1372; vol. 70, No. 4.
Lo et al; Impedance Analysis of MDCK Cells Measured by Electric Cell-Substrate Impedance Sensing; Biophysical Journal; Dec. 1995; pp. 2800-2807; vol. 96.
Ma et al; An Extracellular Cu2+ Binding Site in the Voltage Sensor of BK and Shaker Potassium Channels; The Journal of General Physiology; Apr. 28, 2008; pp. 483-502.
Miyamoto et al.; Na Conductance Kinetics in the Low-Frequency Impedance of Isolated Snail Neurons; IEEE Transactions on Biomedical Engineering; Jul. 1986; pp. 644-653; vol. BME-33.
Rabbitt et al.; Evidence of Piezoelectric Resonance in Isolated Outer Hair Cells; Biophysical Journal; Mar. 2005; pp. 2257-2265; vol. 88.
Rahman et al; A Micro-Electrode Array Biosensor for Impedance Spectroscopy of Human Umbilical Vein Endothelial Cells; Sensors and Actuators B; 2006; pp. 115-120; vol. 118.
Rahman et al; Cell Culture Monitoring by Impedance Mapping Using a Multielectrode Scanning Impedance Spectroscopy System (CellMap); Physiol. Meas.; 2008; pp. S227-S239; vol. 29.
Ratanachoo et al.; Detection of Cellular Responses to Toxicants by Dielectrophoresis; Biochim Biophys Acta.; Aug. 31, 2002; pp. 449-458; vol. 1564, No. 2.
Sohn et al; Capacitance Cytometry: Measuring Biological Cells One by One; PNAS; Sep. 26, 2000; pp. 10687-10690; vol. 97, No. 20.
Stuhmer et al; Electrophysiological Recordings from Xenopus Pocytes; Methods in Enzymology; 1992; pp. 319-339; vol. 207.
Werdich et al; A Microfluidic Device to Confine a Single Cardiac Myocyte in a Sub-Nanoliter Volume on Planar Microelectrodes for Extracellular Potential Recordings; Lab Chip; 2004; pp. 357-362; vol. 4.
Yang et al; Design and Preliminary Evaluation of a Portable Device for the Measurement of Bioimpedance Spectroscopy; Physiol. Meas.; 2006; pp. 1293-1310; vol. 27.
Yang et al; How Does the W434F Mutation Block Current in Shaker Potassium Channels?; J.Gen. Physiol; Jun. 1997; pp. 779-789; vol. 190.

\* cited by examiner

MONITORING MEMBRANE-BOUND PROTEINS

RELATED APPLICATIONS

The present application claims the benefit of U.S. Provisional Patent Application No. 61/517,809, filed on Apr. 25, 2011, which is incorporated herein by reference in its entirety.

This invention was made with government support under grants #DC004928 and #DC006685 awarded by the National Institutes of Health. The Government has certain rights in the invention.

BACKGROUND

The membrane of a cell is a complex structure that both maintains the intracellular milieu and regulates the interaction between intracellular and extracellular space. A major aspect of a cell's physiological state at any given time is the state of its electrochemical equilibrium. In this regard, the membrane acts as a complex electrical component, exhibiting both capacitive and resistive elements whose respective values change in response to electrical stimuli, chemical stimuli, protein expression in the membrane and the cell's native physiological activities. While capacitance of the cell membrane is largely due to the passive dielectric properties of the lipid bilayer, a detectable component of the capacitance also arises from membrane-bound proteins and their dynamic behavior. Dynamic detection of charge displacement in electrically excitable cell membranes can provide biophysical insight into the activity of voltage-sensitive and chemical-sensitive biophysics/physiology of membrane-bound proteins. Accordingly, monitoring membrane dielectric properties can be informative in the study of membrane-bound protein function, wild type and genetic mutations, and respective protein-drug interactions.

DETAILED DESCRIPTION

Reference will now be made to the exemplary embodiments of the present technology, both those described and those illustrated in the drawings, and specific language will be used herein to describe the same. It will nevertheless be understood that no limitation of the scope of the described concepts is thereby intended. Alterations and further modifications of the inventive features illustrated herein, and additional applications of the principles as illustrated herein, which would occur to one skilled in the relevant art and having possession of this disclosure, are to be considered within the scope of the present technology.

In describing and claiming the present technology, the following terminology will be used in accordance with the definitions set forth below.

The singular forms "a," "an," and, "the" include plural referents unless the context clearly dictates otherwise.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Frequencies, amounts, voltages, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the term "about" shall expressly include "exactly," consistent with the discussion above regarding ranges and numerical data.

The term "membrane" refers to the lipid-rich partition separating one cellular or ionic compartment from another including the full complement of lipid bilayer(s), proteins, interacting ions, interacting proteins, and other biomolecules. Examples of membranes include the plasma membrane of an animal cell, the mitochondrial membrane, bacterial membrane, plant cell membrane, liposome membrane and the like.

Reference to a "state" of a protein in the following discussion refers to any condition or characteristic of the protein that is ascertainable using methods or apparatus described herein, including the presence of the protein, as well as its conformation or function.

The term "delivery" as used herein in reference to electrical signals or fields refers to any role in providing or propagating such signals or fields. For example, delivery of an electrical signal into a medium can include emission of the signal into said medium, as well as providing a point at which the signal exits the medium.

Electrically or chemically induced changes ("excitable changes") in integral-membrane protein structure/function result in small but measurable changes in membrane dielectric properties. These changes, associated with excitable charge redistribution and electrical charge mobility, are difficult to monitor using available techniques. Conventional glass/quartz pipette-based electrophysiological techniques, for example, have a sizeable tray capacitance that imposes frequency-dependent limitations on recordings. Herein are introduced technology, techniques and apparatus that bypass these bandwidth limitations to provide novel data pertaining to the biophysics of membrane-protein structure and function. This includes apparatus with sufficient sensitivity to detect small dielectric effects from membrane protein events, including those that are non-conductive.

In accordance with the present technology, monitoring techniques and apparatus can use radio frequency (RF) interrogation between extracellular electrodes to monitor voltage-dependent charge displacement associated with membrane-bound proteins. Specifically, the present invention uses extracellularly applied RF signals to monitor excitable (e.g. electrically or pharmacologically induced) changes in the membrane of a cell expressing exogenous or endogenous proteins. More specifically, the charge associated with the membrane-protein complex displaces within the electric field in response to an applied stimulus, and the corresponding change in RF charge displacement manifests as a measurable change in RF membrane capacitance. These measurements reveal changes in membrane—protein charge arrangement and/or protein—membrane complex mobility and thereby can be used to interrogate drug-protein interactions and protein function.

Turning now to the FIGS., it is noted that reference numerals are not discussed expressly in each figure, but when the same reference numeral is used in more than one figure, but not discussed in each of the relevant figures, that reference numeral should be considered to be of the same or similar structure. Regarding FIG. 1 specifically, an apparatus 100 according to an embodiment is shown in cross-section. A chamber 10 is configured to hold and present a cell 12 to be tested. An insulating partition 14 extends across the chamber so as to divide the space therein into an upper well 16 and a lower well 18. A pore 20 penetrates the insulating partition, providing the only direct communication between the wells. The pore has a shape and size so as to fit snugly around a cell meridian 22 of the cell placed within the pore. Specifically, the pore can have a diameter that is slightly less than that of the cell meridian, so as to provide a tight fit without damaging the cell. This tight fit serves two functions. One is that the cell is held stationary within the chamber by the pore and thereby accessible to subsequent manipulation steps. The tight fit also enables the cell to effectively plug the pore, so that when the cell is in place there is little to no fluid communication between the upper well and lower well. Rather, in this arrangement, the essentially sole electrical pathway in the chamber between the wells is substantially through the cell itself.

Figure 1:
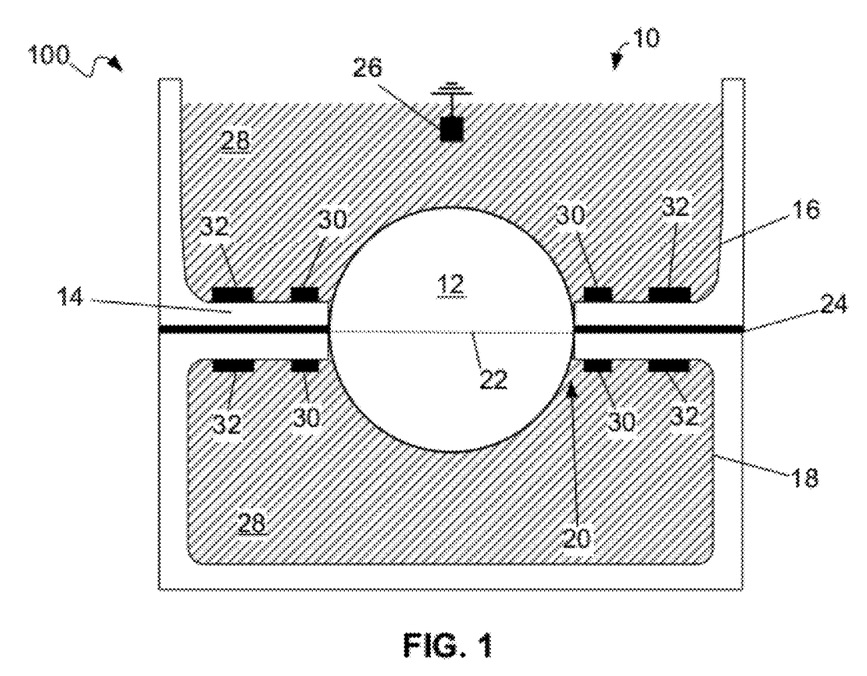
FIG. 1 is a cross sectional view of a cell situated in an apparatus in accordance with an embodiment.

The pore diameter can be selected so as to provide a snug fit around with cells of a given size. In an embodiment, the pore can have a diameter of from about 5 μm to about 2000 μm. The size and robustness of *Xenopus* oocytes make them a useful and commonly-used model for investigating receptor biochemistry and signal transduction. In addition, their capability to translate and express exogenous genetic material makes them a useful expression system to study protein function related to disease and pharmacological action. Accordingly, in one example, the apparatus can include a pore sized to fit *Xenopus* oocytes, i.e. from about 0.8 to about 1.2 mm. HEK 239 cells are another example of a cell line which is able to express exogenous protein in its membrane, could also be used in the apparatus having a pore size from about 10 μm to about 16 μm. Other cell lines that are suitable for the purpose of expressing exogenous proteins in their membranes can be examined with apparatus having appropriately sized pores. Ex-vivo harvested cells can also be examined in accordance with the present technology.

The apparatus further includes a belt electrode 24 located within the insulating partition 14 and situated directly adjacent the pore, and also substantially encircling the pore. In an aspect of the embodiment, this electrode is part of a radio frequency interrogating circuit configured for delivery of RF interrogating signals to a cell placed in the pore. As such, the belt electrode can be situated and have an inner diameter so as to be in contact with or in sufficient proximity to the cell for establishment of an effective field strength in and around the cell. In an aspect, the inner diameter of the belt electrode is such that the belt electrode constitutes at least part of the inner perimeter of the pore 20, and actually participates in creating a snug fit with the cell.

In one aspect, the belt electrode can be functionally connected to a radio frequency signal source (not shown). A separate electrode 26 can be placed in the chamber to serve as the other terminus for the RF field. In one embodiment, the separate electrode can be located above the cell in the upper well as shown in FIG. 1, to interrogate the cell membrane facing the upper well. However, a separate electrode 26 can also be placed in a corresponding position in the lower well to interrogate the cell membrane facing the lower well. The two chambers may contain different chemical compositions or voltages thus allowing measurement of the membrane facing the top (test) well relative to the bottom (control) well for a single cell and experiment. RF interrogating electrodes can also be in any other location in the chamber so as to provide a desired field strength and/or geometry.

In another embodiment, the belt electrode 24 can be grounded and RF signals can be passed from electrode 26 or other electrodes around the cell to the belt electrode. A virtual ground circuit can be used on the belt electrode, or any other electrode, to measure the RF current. RF voltage dropped across the chamber can simultaneously be measured using two other electrodes, including those located on the surfaces of the insulating partition. RF current and voltage information can then be used to estimate changes in chamber RF impedance values.

In an aspect, the chamber of the apparatus is configured to hold one or more media 28, such as ionic liquid media, that facilitate maintenance of the cell, delivery of stimuli, and/or provide electrical communication among components. When a cell is in place in the pore 20, the upper well 16 and lower well 18 can constitute two separate fluid environments. In one approach, the same medium can be placed in both wells. Alternatively, the preparation allows for the two wells to contain different media.

In accordance with the embodiment, the apparatus 100 can further include electrodes and other circuitry elements for signal delivery and measurement. In a particular embodiment, a measuring circuit is included for measuring RF impedance presented by the cell ($Z_{RF}$). In a more particular example, the measuring circuit of the apparatus comprises two or more voltage sensing electrodes 30 situated for effective measurement of RF voltage in addition to the RF current delivering and measuring electrodes, thus allowing direct measurement of the impedance of the upper or, independently, the lower portion(s) of membrane using the RF interrogating signal.

In an embodiment, the apparatus is equipped to provide an electrical stimulus to the cell for probing voltage-dependent changes in membrane displacement currents and capacitance. In a particular embodiment, the apparatus includes electrodes for directly manipulating the local membrane potential of the cell. In a more specific embodiment, two extracellular current passing electrodes are used to pattern an approximately constant electric field across the membrane, thereby effectively providing voltage-clamp functionality. In one embodiment the apparatus and method allows the membrane potential facing the upper well to be specified at a level nearly equal and opposite to that on the membrane facing the lower well. In this embodiment, the voltage in the upper well is controlled relative to the lower well, with the intracellular voltage floating to the average, thus specifying nearly equal and opposite electric fields across the portions of the membrane facing the upper and lower wells respectively. For example, a current injecting electrode 32 can be used to pattern an electric field across the cell membrane in conjunction with the grounded belt electrode 24 to impose the stimulus voltage. In one implementation, illustrated in FIG. 2, the current injecting electrode 32 can be employed in conjunction with the belt electrode 24 (which is grounded in this implementation) to deliver an RF interrogating field 34 to the cell. In this implementation, during RF interrogation these same electrodes also pattern an electric field ($V^+$, $V^-$) across the cell, imposing opposite voltages ($E^+$, $E^-$) across regions of the cell membrane facing the upper well and the lower well. (It should be noted that to preserve visual clarity in this figure, the medium is not shown, and also for elements present in both wells only the counterparts in the lower well are labeled.)

Figure 2:
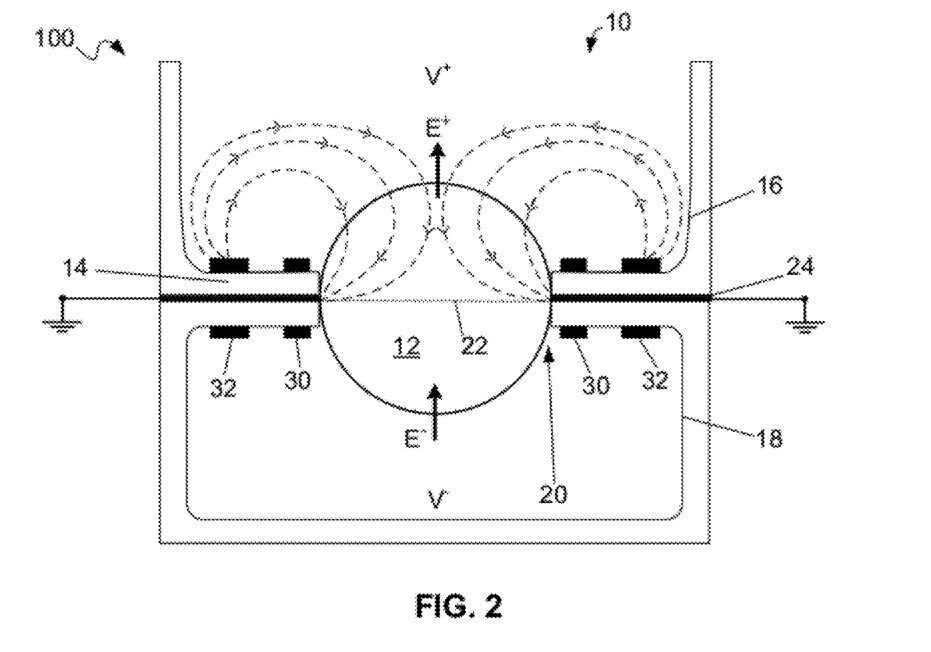
FIG. 2 is a cross sectional view showing radio frequency (RF) interrogation and stimulation of a cell in an apparatus in accordance with an embodiment.
Figure 3A:
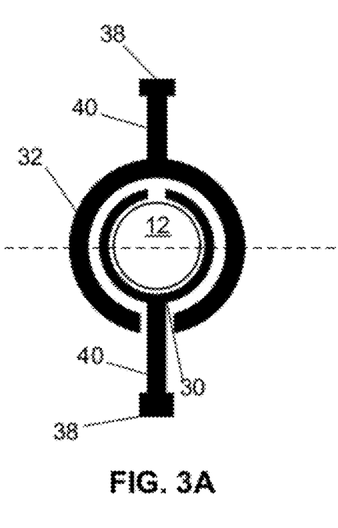
FIG. 3A is a top view of part of the apparatus of FIG. 1.
Figure 3B:
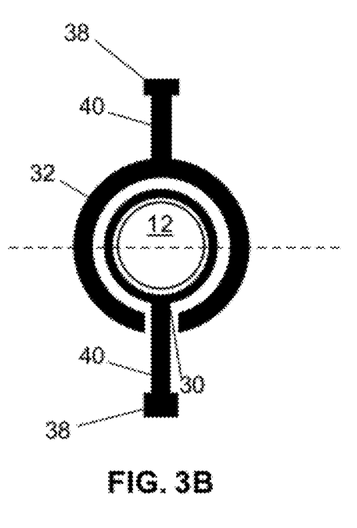
FIG. 3B is a top view of part of an apparatus in accordance with another embodiment.

Referring again to FIG. 1, the current injecting electrode 32 and voltage-sensing electrodes 30 can be patterned onto the insulating partition 14 adjacent to the pore 20. In a specific aspect, the electrodes are shaped and situated so as to substantially encircle the pore. FIGS. 3A and 3B show a top view of a stimulus/RF interrogation circuit as in FIG. 1 (the dashed line indicates the level at which the cross section of FIG. 1 is taken.) As shown in FIG. 3A, one or both of the voltage clamp electrodes can be partially annular. Alternatively, one or both electrodes can be fully annular. Alternatively still, the electrodes can have other shapes and configurations that are suitable based on the geometry of the apparatus or of the desired electrical field. As shown in FIG. 3B, the electrodes can be arranged concentrically around the pore, and comprise an annular electrode located centrally with respect to a partially annular electrode. In one example, as also shown in FIGS. 1, 2, 3A, and 3B, the RF voltage sensing electrode 30 is located nearest to the pore, with the current injecting electrode 32 being larger and located peripherally relative to the voltage sensing electrode and the pore. However it is contemplated that other arrangements of these electrodes will be suited to providing extracellular voltage clamp or RF delivery in the present apparatus.

Figure 4:
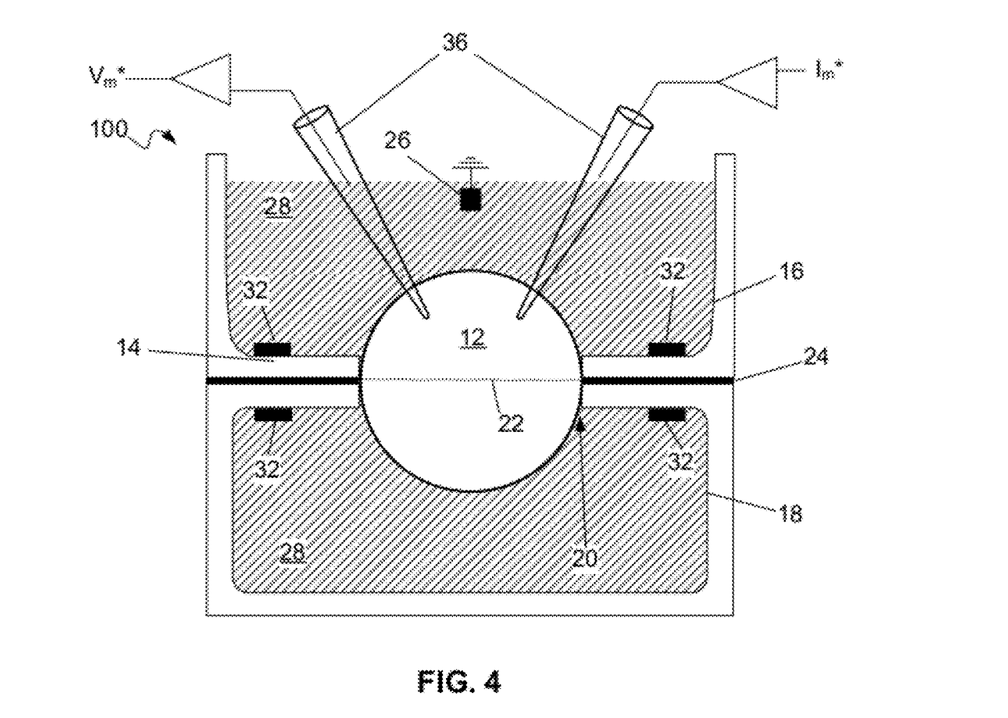
FIG. 4 is a cross sectional view of a cell situated in an apparatus in accordance with an embodiment.

In a particular embodiment, the extracellular voltage clamp/RF delivery circuit can comprise a plurality of electrode pairs. As shown in FIGS. 1 and 2, a first current injecting electrode and a first voltage sensing electrode can both be located on a surface of the insulating partition so as to be in contact with the medium 28 in the upper well 16, and a second current injecting electrode and a second voltage sensing electrode can both be located on a surface of the insulating partition so as to be in contact with the medium in the lower well 18. If the annular belt electrode 24 that surrounds the median of the cell is connected to electrical ground, these two sets of voltage clamp electrodes can be operated separately to provide stimuli in one or the other wells. Furthermore, in an alternative embodiment, voltage clamp or other electrical stimulus delivery can be provided by inserting conventional glass micropipette electrodes 36 into the cell, as shown in FIG. 4, while simultaneously using the extracellular electrodes for RF impedance change measurements only. Different pairs of electrodes can also be used to evaluate the RF impedance properties of the whole cell or of varying portions of the membrane-protein complex.

The electrodes and other circuitry of the apparatus can be connected to external components as desired to provide functionality to the apparatus. Examples of such components include without limitation amplifiers, signal generators, signal conditioners, data recorders, stimulus isolation units, monitors, oscilloscopes, and the like. Referring again to FIGS. 3A and 3B, in one aspect a functional interface with external components is provided by bond pads 38 situated so as to be accessible for this purpose. Connection between the operative surface of the electrode and the bond pad can be provided by electrical traces 40. For example, traces can be patterned to connect centrally located electrodes of the multiple layered electrode array to peripherally located bond pads.

The electrodes and/or traces can be substantially covered by an overlying insulation layer provided to protect the electrodes and enhance signal integrity. These structures can be patterned on a surface in the chamber, e.g. on a surface of the insulating partition. Alternatively, any of the structures can be provided in a dedicated layer of a multilayered fabrication arrangement. For example, the electrode array and insulating partition can comprise a plurality of metalized layers separated by insulating layers, with one layer for each set of voltage clamp/RF electrodes, and disposed on opposing surfaces of a layer providing the belt electrode.

The chamber, partition, and electrode layers of the apparatus can be fabricated by rapid-prototyping, microfabrication, thick film technology, and electrochemical techniques known to the pertinent arts. The arrangement of electrodes, vias, bond pads and the like may be designed using computer-aided design software, and can be patterned onto their respective substrates using suitable conductive metals such as gold, copper, platinum, or combinations thereof. Any substrate material suitable for supporting electronic circuitry can be used to support the conductive elements. The electrodes in contact with the cell or media surrounding the cell can be plated with a biocompatible material that include platinum, iridium, PEDOT, gold or any other material useful for electrical interrogation. In a particular aspect, a non-conductive material, e.g. a polyester or polyimide, is used for fabricating the chamber and insulating layers so as to provide resistive electrical isolation and reduced capacitance between electrical elements and between the wells.

Figure 5A:
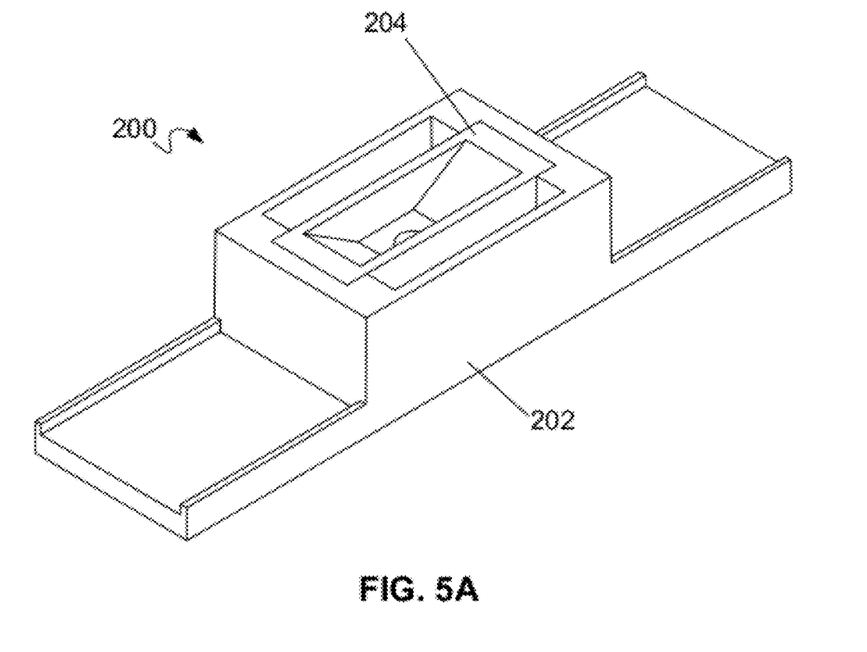
FIG. 5A is a perspective view of a platform housing for an apparatus in accordance with an embodiment.

The apparatus can be machined out of a body of a suitable material (e.g. polycarbonate or polyacrylic materials) or fabricated by other means, so as to provide the structures and spaces described above. In addition, the apparatus can comprise a plurality of modules that can be separated so as to provide access to the lower surfaces and spaces of the apparatus. In one example as shown in FIG. 5A and in exploded view in FIG. 5B, a platform 200 can comprise two different components. A larger bottom chamber 202 can include a hollow space 204 to define at least part of the bottom well. The top edges of this component can be used to suspend a second, smaller top chamber 206. This component of the platform can include a hollow space 208 to define the upper well. In a particular aspect, a multilayer-electrode array structure can be clamped in the upper chamber. The upper chamber can also provide space above the level of the upper well that is not filled with an electrically conductive solution to accommodate bond pads for connection with the electrode arrays.

Figure 5B:
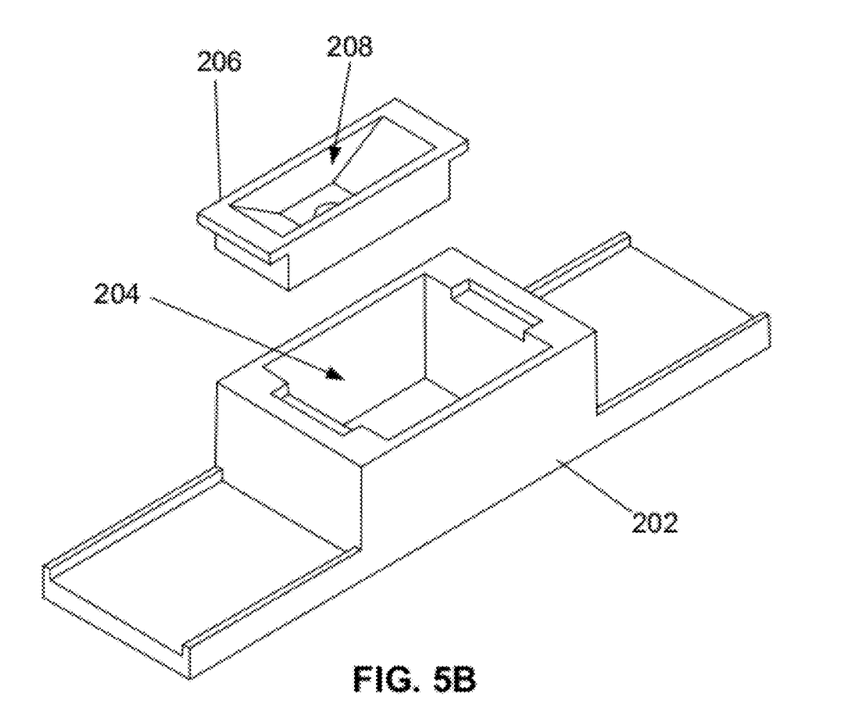
FIG. 5B is an exploded view of the platform of FIG. 5A.
Figure 6A:
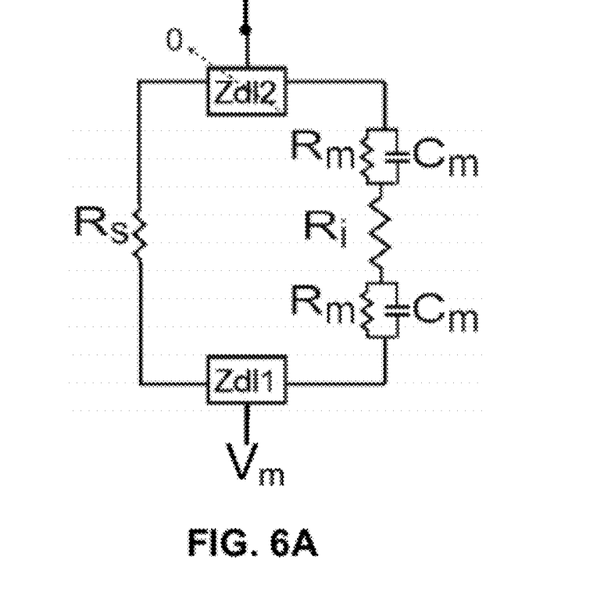
FIG. 6A is a lumped parameter model of impedances presented by a cell and apparatus to radio frequency interrogation.
Figure 6B:
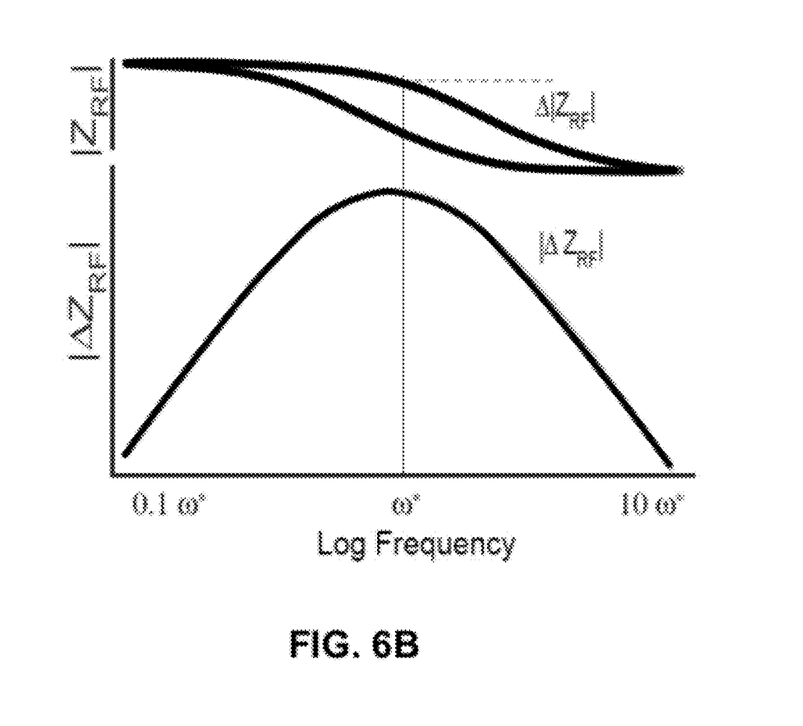
FIG. 6B is a graph describing a relationship between RF signal frequency and changes in cell membrane impedance.

FIG. 6A shows a simple lumped parameter model approximating the impedances involved in electrical interrogation of a cell in an apparatus according to the present technology. These include the shunt resistance ($R_s$), membrane impedance ($Z_m$), intracellular resistance ($R_i$), and electrode double layer ($Z_{dl}$). Such a model can be used to estimate the magnitude of RF impedance change expected to occur for a small change in effective membrane capacitance. RF impedance ($Z_{RF}$) decreases with increasing RF frequency as shown in FIG. 5B. As also shown in FIG. 5B, over a range of middle frequencies (i.e. about 0.1 MHz to about 3.0 MHz), given changes in membrane capacitance results in maximal changes in $Z_{RF}$. At frequencies below the RC corner frequency of the membrane, the RF impedance is dominated by the conductive shunt path around the cell, making these frequencies less effective for measuring changes in membrane impedance. Furthermore, the RC corner frequency is higher for large shunt conductances (e.g. up to about 5 MHz). Conversely, decreasing shunt conductance decreases the corner frequency, thereby reducing the effect of this component at optimal interrogation frequencies.

As discussed above, in the present apparatus the pore provides a tight fit around the cell. The resulting strong electrical contact between the belt electrode and the cell greatly reduces the shunt conductance available to the RF signal current. Reduction of the shunt conductance in turn lowers the corner frequency of the membrane, making low frequency RF signals suitable and effective for visualization of slight changes in membrane capacitance. As such, the present apparatus provides for impedance measurement that is sufficiently sensitive to ascertain small changes in membrane dielectric, such as those that result from charge displacements associated with a state change of membrane proteins. Accordingly, in one aspect, an RF signal is used for which changes in the state of the protein produce substantially maximal changes in the RF impedance. In another aspect, the RF signal has a frequency of from about 0.1 MHz to about 50.0 MHz. In a particular example, the RF signal has a frequency of from about 0.2 MHz to about 2.0 MHz. In a more particular example, the RF signal has a frequency of from about 0.4 MHz to about 0.6 MHz. In a specific example, the RF signal has a frequency of about 0.5 MHz. The RF interrogating signal can comprise a single frequency or a plurality of frequencies in one of these ranges. In one aspect, the signal can comprise a discrete number of frequencies, presented simultaneously or in a particular temporal pattern. The frequencies can be selected deliberately or at random. In another aspect, the RF signal can comprise a continuous frequency sweep.

The present technology makes possible methods for monitoring membrane-related cellular phenomena. In accordance with an embodiment, a method of examining membrane-bound proteins in a cell can comprise placing a medium in the wells of an apparatus as described herein and placing a cell in the pore of an so as to establish a snug fit between the cell and the pore. Cell placement can be accomplished using handling techniques known in the art. In a particular example suction can be applied to one of the wells in order to draw the cell securely into the pore. After securely situating the cell in the pore, the composition of media in the bottom and top half of the wells can be altered by using a standard perfusion system. The cell is then interrogated by delivering a radio frequency signal into the medium while simultaneously delivering a stimulus (e.g. voltage-clamp or pharmaceutical agent) to the cell. In one implementation of this technique, the stimulus can be an extracellularly applied stimulus voltage that changes the membrane potential inside of a cell. In one aspect an RF signal frequency is used for which changes in the state of the protein produce substantially maximal changes in the RF impedance. This value will depend on the specific configuration of the electrodes around the cell. In one embodiment of the technique, the RF signal has a frequency of from about 0.1 MHz to about 50.0 MHz. In a particular example, the RF signal has a frequency of from about 0.2 MHz to about 2.0 MHz. In a more particular example, the RF signal has a frequency of from about 0.4 MHz to about 0.6 MHz. In a specific example, the RF signal has a frequency of about 0.5 MHz. The RF interrogating signal can comprise a single frequency or a plurality of frequencies in one of these ranges. In one aspect, the signal can comprise a discrete number of frequencies, presented simultaneously or in a particular temporal pattern. The frequencies can be selected deliberately or at random. In another aspect, the RF signal can comprise a continuous frequency sweep.

By allowing for the detection of charge displacement associated with membrane-bound proteins, the method provides a way to investigate the types of voltage-responsive proteins expressed by a cell as well as the activity of such proteins. In one specific implementation of the technique, a specific protein type can be evaluated by expressing a particular protein in a cell line known for exogenous protein expression. This examination can be facilitated by changing the membrane potential so as to induce voltage-dependent protein activity during RF interrogation. Accordingly, the method can include delivering a step voltage stimulus, or another incremental waveform, via a voltage clamp circuitry such as described above. In addition, the electrodes of the apparatus can also be employed to deliver other electrical stimuli. In one example, interrogation of the cell can be done in conjunction with imposition of a DC electrical field across the cell.

Another aspect of the present technology is the ability to probe responses of membrane-bound proteins to agents suspected of interacting with such proteins. Accordingly, the concepts described herein also provide a method of testing pharmacological agents by using an apparatus as described above to interrogate a cell having putative target proteins for the agent. In one embodiment, a stimulus delivered to the cell can include introduction of a pharmacological agent into one of the wells in connection with RF interrogation. This can be utilized in conjunction with electrical stimuli such as voltage clamp or imposition of DC fields.

EXAMPLES

Example 1

Monitoring Voltage-Dependent Impedance Change in *Xenopus* Oocytes Using RF Interrogation Ooocyte Protein Expression Complementary deoxyribonucleic acid (cDNA) for the Shaker ion-channel variant ShakerB-IR (inactivation removed) was transformed in *E. coli* and linearized using the restriction enzyme, Kpn-1. cRNA was transcribed from linearized DNA, and 32 nL/cell of the transcribed RNA was injected into *Xenopus* oocytes. Recordings were done 24-48 hours after injection to allow time for protein expression. Currents were measured using two-microelectrode voltage clamp to verify ShakerB-IR ion channel expression. Oocytes were stored in Superbarths Oocyte media (88 mM NaCl, 1 mM KCl, 0.41 mM CaCl2, 0.33 mM Ca(NO3)2, 1 mM MgSO4, 2.4 mM NaHCO3, 10 mM HEPES, 1 mM pyruvate and 50 μg/ml gentamicin, titrated using NaOH to a pH of 7.4) at 17° Celsius (C.). Oocytes were also bathed in this media during RF recording.

Recording from Oocytes under Voltage Clamp with RF Interrogation

Oocytes were positioned into a recording chamber consisting of an RF belt electrode surrounding the meridian of the cell and a ground electrode located in the oocyte media above an axial pole of the cell. Two glass micropipettes (1-3 MΩ access resistance) filled with 3M KCL were carefully guided into the oocyte using an upright microscope (Zeiss Axio-Tech). One micropipette was attached to a voltage-measuring headstage (HS-2Ax1 LU, Molecular Devices, Sunnyvale, Calif.) and the second micropipette was attached to a current-injecting headstage (HS-2Ax10MGU, Molecular Devices, Sunnyvale, Calif.). These pipettes, in addition to a voltage-driving amplifier, were used to control low frequency (~DC steps) two-electrode voltage clamp in an oocyte (AxoClamp2B, Molecular Devices, Sunnyvale, Calif.). Each oocyte was held at a −90 mV (holding potential) and was remotely commanded to three potentials using voltage-clamp software: −120 mV, −30 mV and +40 mV (Patchmaster, HEKA Inst., Bellmore, N.Y.). Voltage-command sequences were applied to cells between 50-200 times and responses were averaged to improve the signal/noise (S/N) ratio in the electrode current and, more importantly, the RF lock-in data. An on-board voltage divider circuit was used to measure the RF current and voltage. The RF source outputted a 300 mV (0-peak), randomized sinusoidal voltage (300 kHz, 500 kHz or 1 MHz; AFG320, Tektronix, Beaverton, Oreg.). Voltage measurements were made relative to an Ag/AgCl ground wire placed ~5 mm above the cell in recording chamber media. This ground was common for both the RF and TEVC measurements.

RF voltage measurements were sampled through a headstage voltage-follower operational amplifier (OPA356, Texas Instruments, Dallas, Tex.). The RF signal was high pass filtered (100 kHz, 48 DB/oct Bessel HPF; SIM965, Stanford Research Systems, Sunnyvale, Calif.) and detected by a lock-in amplification (0 integration time, SR844, Stanford Research Systems, Sunnyvale, Calif.). The quadrature outputs on the lock-in amplifier detected changes on the order of 10 microvolts, and time delays caused by the lock-in amplifier and HPF were accounted for prior to data analysis. TEVC data (command voltage, sensed voltage, measured current) and RF data (quadrature outputs from the lock-in amplifier) were sampled every 20 μs using a 16 bit A-D converter (ITC-18, HEKA Inst. Bellmore, N.Y.).

Results

Figure 7:
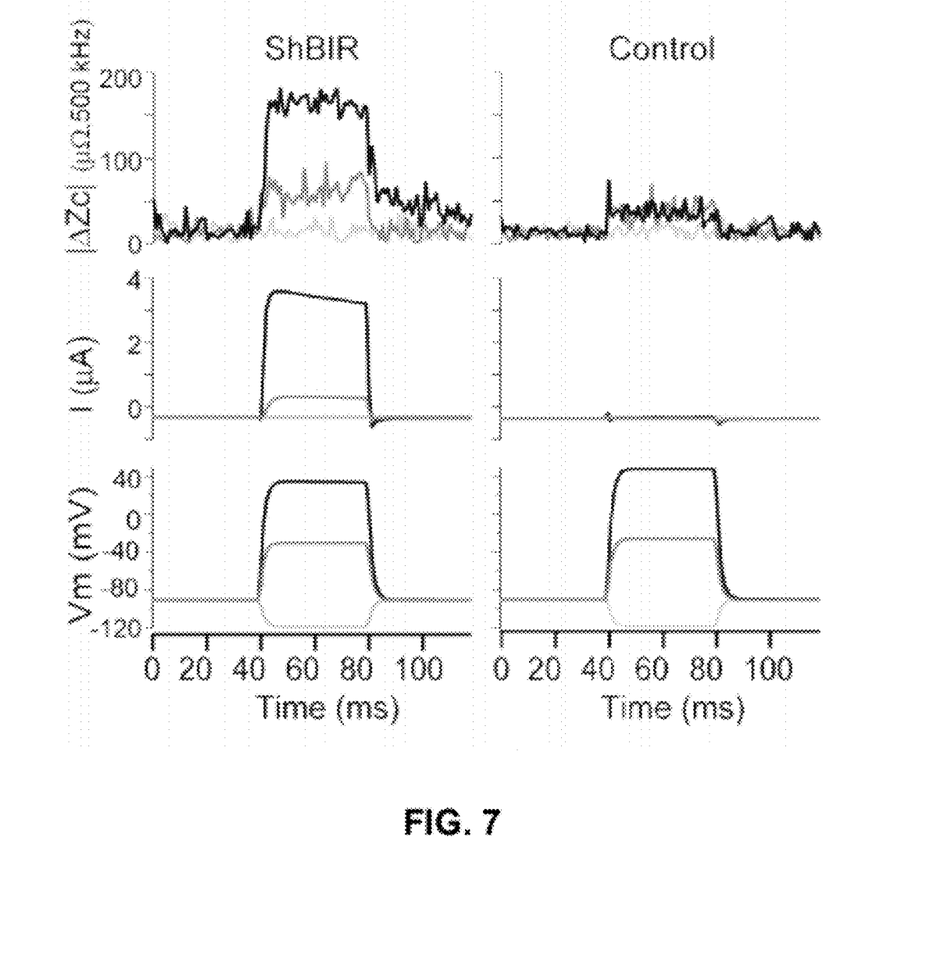
FIG. 7 shows millisecond resolution of change in cell membrane capacitance ($|\Delta Zc|$) in oocytes in response to voltage clamp excitation.

FIG. 7 shows ShakerB-IR (n=5, control: n=6) change in RF impedance |Δ Zc| collected using 500 kHz interrogation for depolarized (black line, ~40 mV), slightly depolarized (dark gray line, −28 mV) and hyperpolarized (gray line, ~−120 mV) membrane potentials. Membrane current (I) and voltage ($V_m$) were monitored using conventional TEVC for both ShakerB-IR and control oocytes. ShakerB-IR injected oocytes achieved a 3 μA current at the 40 mV depolarization (black line), as expected. Control oocytes did not exhibit significant currents during depolarization. |Δ Zc| and ionic current increased nonlinearly in Shaker expressing oocytes.

Figure 8:
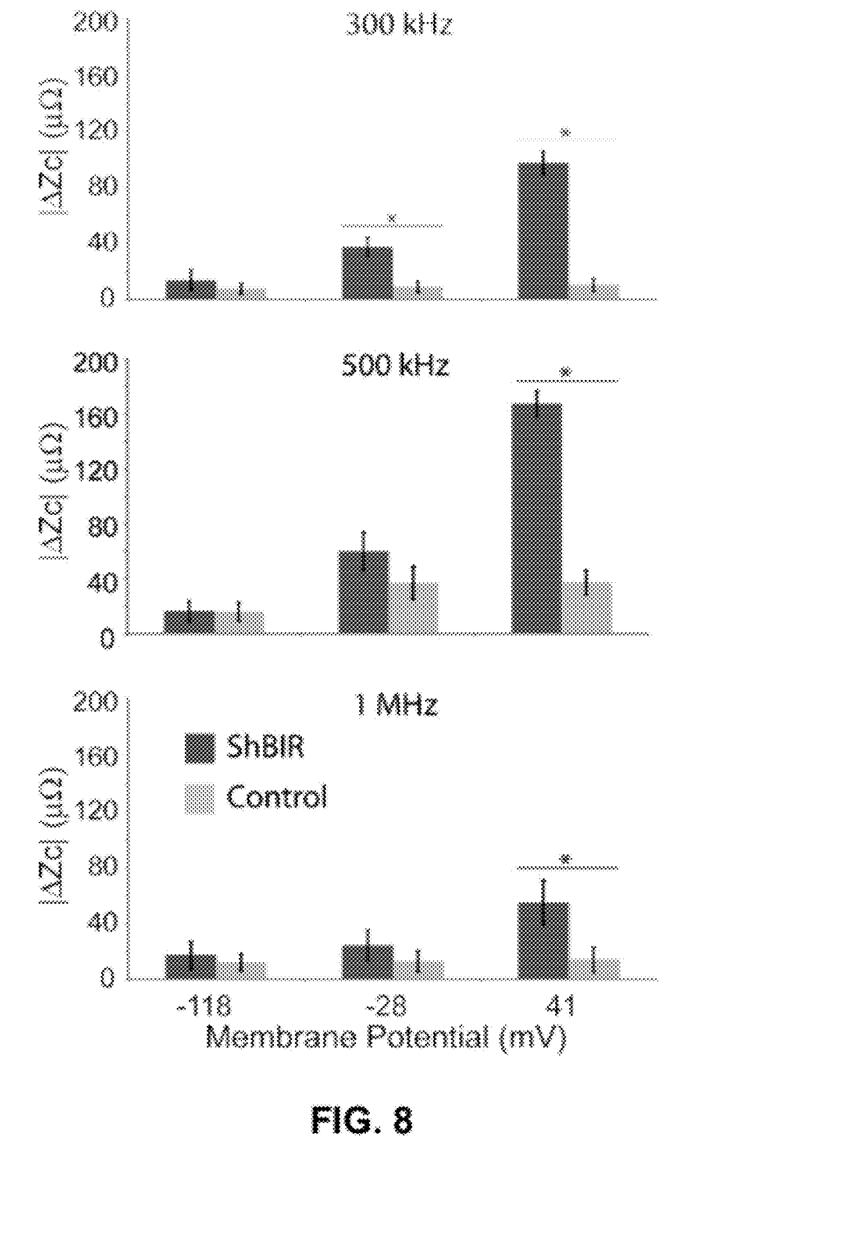
FIG. 8 shows steady state values of $|\Delta Zc|$ for different membrane potentials.

The steady-state (at 60-80 ms in FIG. 7) change in RF impedance (|Δ Zc|) is summarized for 300 kHz, 500 kHz and 1 MHZ interrogation frequencies in FIG. 8. Impedance changes are relative to the RF impedance measured at the −90 mV holding potential, and are shown for voltage steps to −118 mV (control: n=7, ShakerB-IR: n=5), −28 mV (control: n=6, ShakerB-IR: n=5) and +41 mV (control: n=7, ShakerBIR: n=5). At the −28 mV voltage step, when the Shaker channel was just beginning to open, a significant increase in steady-state |Δ Zc| was measured at 300 kHz between ShakerB-IR and the control oocytes. Results show statistically significant (*, p<0.05 differences between RF impedance changes in ShakerB-IR vs. control cells at the 41 mV membrane depolarization as well. Hence, opening of ShakerB-IR channels caused an increase in membrane polarization that was detectable with RF interrogation frequencies.

Example 2

Testing Effects of $Cu^{2+}$ on Voltage-Dependent Charge Displacement of Shaker B-IR $K^+$ Ion Channels in *Xenopus* Oocytes Experimental Set-Up Expression of Shaker B-IR ion channels was induced in *Xenopus* oocytes using a similar approach to that described in Example 1. Oocytes were set up in the recording preparation of Example 1. RF interrogation was done using a 500 kHz signal. Oocytes were held at −90 mV (holding potential) for 360 ms, and a voltage step was then applied for 40 ms. Nine different voltage steps were applied to the oocyte (−120 mV, −60 mV, −40 mV, −30 mV, −20 mV, −10 mV, 0 mV, 10 mV, 40 mV), and are collectively referred to hereafter as a voltage train. Voltage trains were applied to each cell 50 times.

In a subset of experiments, ~120 μM $Cu^{2+}$ solution (Copper ICP/DCP standard solution 10,000 μg/mL $Cu^{2+}$ in 2% $HNO_3$, Sigma Aldrich, St. Louis, Mo.) was applied as an ion channel blocker. The $Cu^{2+}$ solution was manually pipetted directly above the cell. The concentration of $Cu^{2+}$ added was approximate, as it depended on the volume of Superbarths oocyte media in the recording chamber (~1.25 mL).

Results

Figure 9:
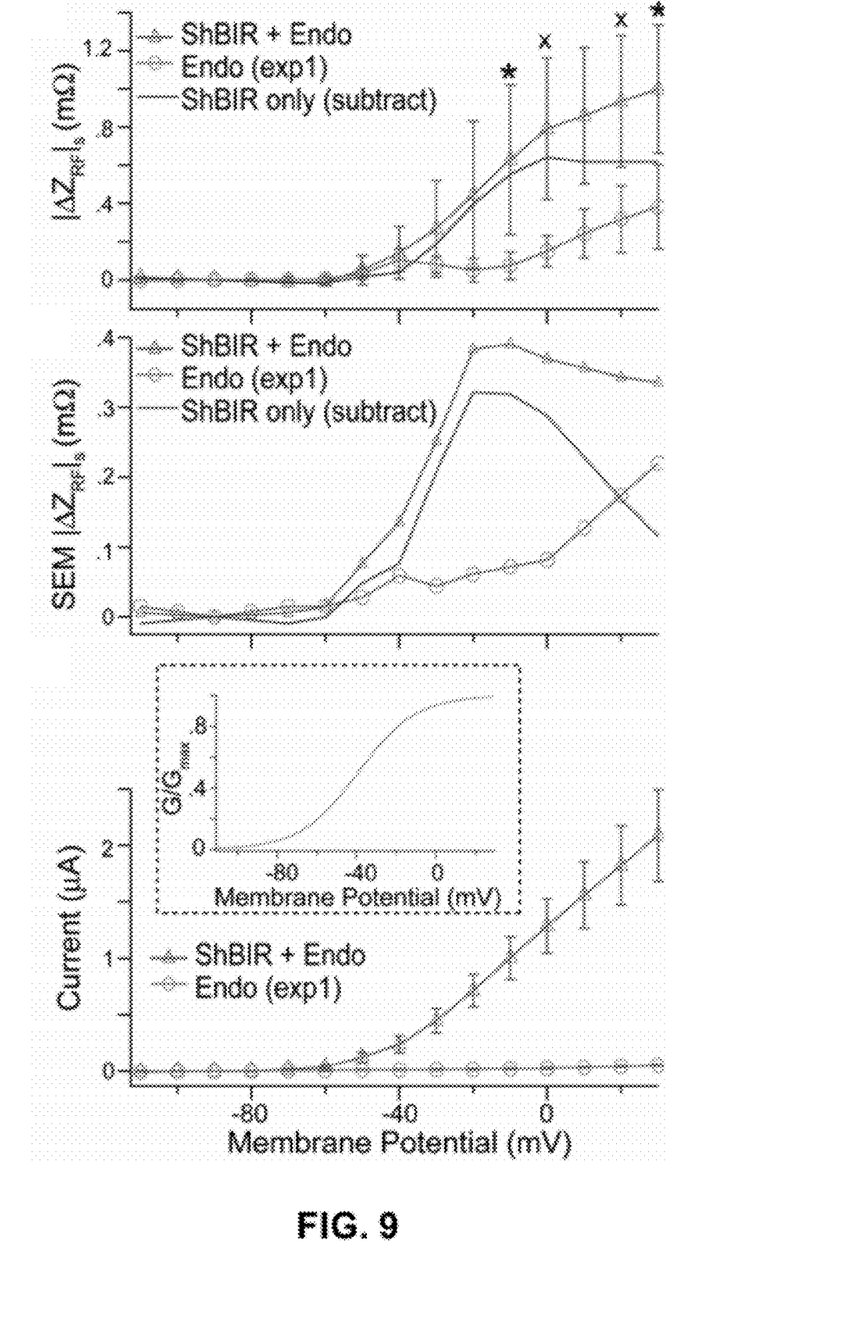
FIG. 9 is a graph of change in RF impedance in oocytes to changing membrane potential.

FIG. 9 (top panel) shows the command-potential dependent change in RF impedance for both control oocytes endogenous protein response, "Endo") and ShakerB-IR expressing oocytes (ShakerB-IR+endogenous protein response, "ShBIR+Endo"). Changes are shown relative to RF impedance at the −90 mV holding potential. As ShakerB-IR has inactivation removed, the results shown here were averaged over a time window 5-40 ms after the command voltage-step. Both the control and ShakerB-IR expressing oocytes showed significant differences in RF impedance relative to the value at the holding potential for command potentials above −20 mV (near the half-activation potential for this ion channel). The difference between the ShakerB-IR and control populations reflects the contribution from ShakerB-IR expression ("ShB-IR only")—a difference that closely followed the open probability and conformation of the channel (cf. top panel vs. bottom panel inset, linear correlation r=0.94). The standard error of the means (SEM) for both control cells and ShakerB-IR expressing oocytes are shown in the center panel of FIG. 9. Subtraction of the control SEM from the ShakerB-IR SEM exhibited a bell-shaped curve, consistent with a larger variance in ShakerB-IR protein displacement currents when channels were poised near their half-activation voltage. The larger variance at the half-activation voltage of the ShakerB-IR channels ("ShB-IR only") was expected, because at this potential, each channel has equal probability to flip between its open or closed state and each state has differing RF displacement currents. Thus, this data reflected the underlying variance of the ensemble of ShakerB-IR proteins.

Figure 10:
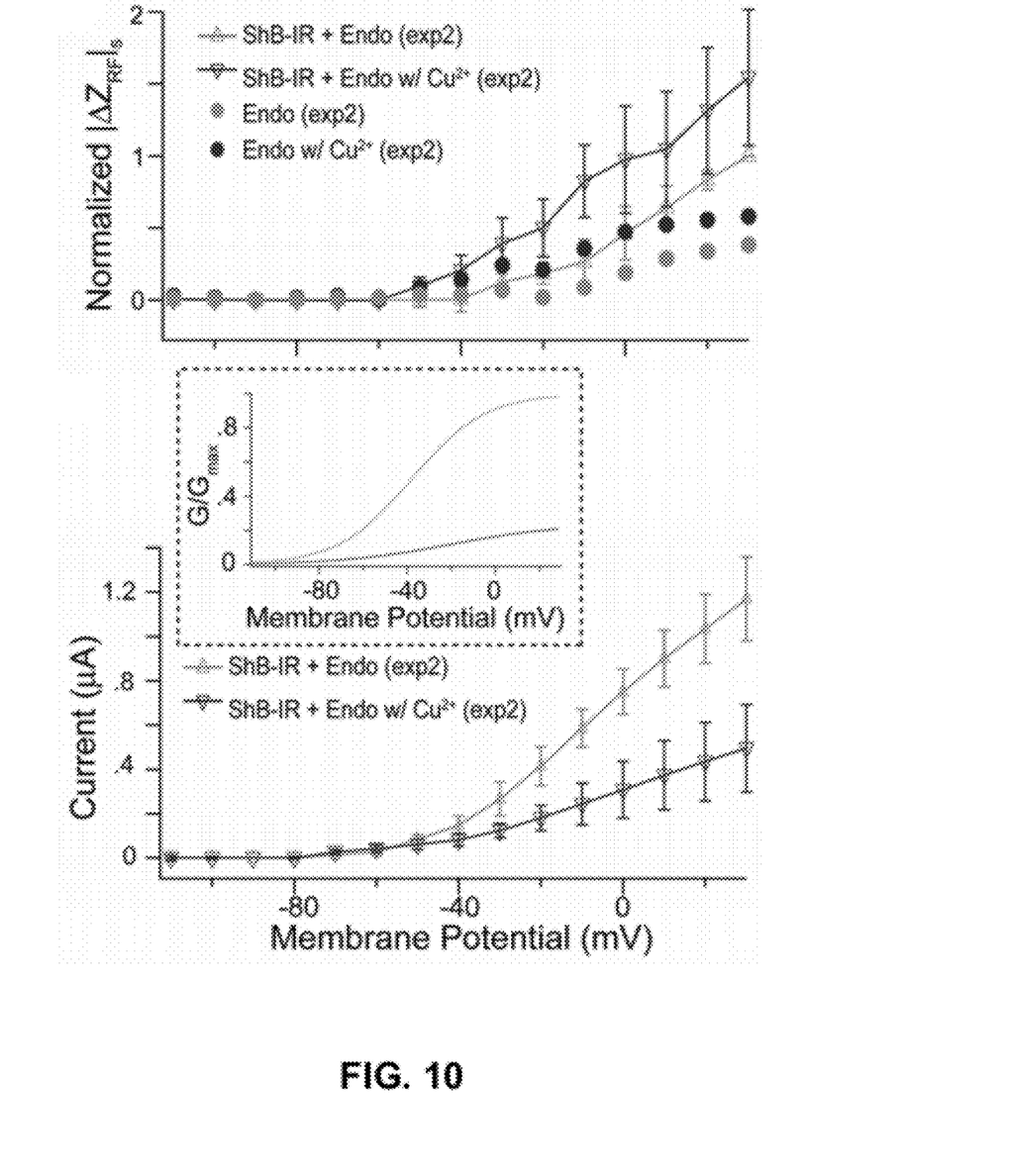
FIG. 10 is a graph showing effects of $Cu^{2+}$ on the change in RF impedance in oocytes to changing membrane potential.

Application of extracellular $Cu^{2+}$ is known to shift the $K^+$ conductance to more depolarized levels and serve as an effective blocker at physiological voltage levels. It was therefore expected that $Cu^{2+}$ would alter voltage-dependent RF impedance. Indeed, results in FIG. 10 show that application of $Cu^{2+}$ blocked the ShakerB-IR $K^+$ current. However, even though the conductance associated with the $Cu^{2+}$ treated ShakerB-IR protein decreased, its interaction with the channel increased charge displacement within the RF electric field. This response was not observed to the same extent in control cells, indicating that $Cu^{2+}$ interacted specifically with the ShakerB-IR $K^+$ ion channel to affect the measured RF response. These results illustrate the power of RF measurements to reveal novel information about molecular interactions with the protein and indicate the pharmaceutical relevance of this technology to investigate drug-protein interactions.

While the forgoing examples are illustrative of the principles of the present technology in one or more particular applications, it will be apparent to those of ordinary skill in the art that numerous modifications in form, usage and details of implementation can be made without the exercise of inventive faculty, and without departing from the principles and concepts described herein. Accordingly, it is not intended that these principles and concepts be limited, except as by the claims set forth below.

What is claimed is:

1. An apparatus for monitoring membrane-bound proteins in a cell, comprising:
   a chamber divided into an upper well and a lower well by an insulating partition;
   a pore penetrating the insulating partition and having a size and shape so as to snugly hold a cell in place between the upper well and lower well;
   a radio frequency interrogating circuit for delivering radio frequency interrogating signals to the cell, including a belt electrode located within the insulating partition and situated directly adjacent to the pore and substantially encircling the pore;
   a current injecting electrode located on a surface of the insulating partition; and
   a plurality of voltage sensing electrodes for measuring the radio frequency impedance of a membrane of the cell, wherein at least one of the plurality of voltage sensing electrodes is located on the surface of the insulating partition,
   wherein changes in the impedance signals presence of a protein in the membrane of the cell and a state of the protein.

2. The apparatus of claim 1, further comprising a plurality of voltage clamp electrodes configured for imposing a stimulus voltage across a region of the membrane.

3. The apparatus of claim 2, wherein the plurality of voltage clamp electrodes are configured so that the stimulus voltage across a region of the membrane facing the upper well has an opposite polarity across a region of the membrane facing the lower well.

4. The apparatus of claim 1, wherein the current injecting electrode substantially encircles the pore.

5. The apparatus of claim 1, wherein the voltage sensing electrode located on the surface of the insulating partition substantially encircles the pore.

6. The apparatus of claim 1, wherein the belt electrode is configured to act as a ground.

7. The apparatus of claim 1, comprising:
   a first current injecting electrode and a first voltage sensing electrode, both located on an upper well surface of the insulating partition;
   a second current injecting electrode and a second voltage sensing electrode, both located on a lower well surface of the insulating partition.

8. The apparatus of claim 1, wherein the radio frequency interrogating signal has a frequency at which changes in the state of the protein produce substantially maximal changes in the impedance.

9. The apparatus of claim 1, wherein the radio frequency interrogating signal has a frequency of from about 0.1 MHz to about 50.0 MHz.

10. The apparatus of claim 9, wherein the radio frequency interrogating signal has a frequency of from about 0.4 MHz to about 0.6 MHz.

11. The apparatus of claim 9, wherein the radio frequency interrogating signal comprises a discrete number of frequencies or a continuous frequency sweep.

12. A method of examining membrane-bound proteins in a cell, comprising:
    using the apparatus of claim 1;
    placing a cell in the pore so as to establish a snug fit between the cell and the pore;
    placing a conductive medium in each of the upper well and lower well;
    delivering a radio frequency interrogating signal into the medium to generate an interrogating electric field across the cell within the pore;
    imposing a stimulus voltage across a region of the membrane of the cell; and
    using the radio frequency interrogating signal to measure impedance of the membrane and thereby ascertain a state of a protein in the membrane.

13. The method of claim 12, wherein the stimulus voltage across a region of the membrane facing the upper well has an opposite polarity across a region of the membrane facing the lower well.

14. The method of claim 13, wherein the stimulus voltage is delivered via an extracellular electrode.

15. The method of claim 12, wherein the stimulus voltage is imposed after introducing a pharmacological agent into at least one of the upper well or the lower well.

16. The method of claim 12, comprising placing different media in the upper well and the lower well.

17. The method of claim 13, wherein the radio frequency signal has a frequency of from about 0.1 MHz to about 50.0 MHz.

18. The method of claim 17, wherein the frequency is from about 0.4 MHz to about 0.6 MHz.

19. A method of testing a pharmacological agent, comprising:
    using the apparatus of claim 1
    placing the cell in the pore so as to establish a snug fit between the cell and the pore;
    placing a conductive medium in each of the upper well and lower well;
    delivering a radio frequency interrogating signal into the conductive medium;
    placing an amount of a pharmacological agent in at least one of the upper chamber and the lower chamber; and
    ascertaining a state and function of a protein in a membrane of the cell by using the radio frequency interrogating signal to measure impedance of a region of the membrane in the well containing the pharmacological agent relative to a region of the membrane facing the other well.

* * * * *